(12) United States Patent
Sharma et al.

(10) Patent No.: US 6,528,257 B1
(45) Date of Patent: Mar. 4, 2003

(54) METHOD FOR THE SIMULTANEOUS MONITORING OF INDIVIDUAL MUTANTS IN MIXED POPULATIONS

(75) Inventors: Vishva Mitra Sharma, New Delhi (IN); Kaliannan Ganesan, New Delhi (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 09/612,555

(22) Filed: Jul. 7, 2000

(51) Int. Cl.⁷ .................... C12Q 1/68; C12P 19/34; C12N 15/87; C12N 15/74
(52) U.S. Cl. .................... 435/6; 435/462; 435/463; 435/473; 435/91.21; 435/91.2
(58) Field of Search .................... 435/462, 463, 435/473, 6, 91.21, 91.2

(56) References Cited

U.S. PATENT DOCUMENTS 5,612,180 A * 3/1997 Brown et al.

OTHER PUBLICATIONS

Sambrook et al. Molecular Cloning a Laboratory Manual Second Edition pp. 8.46–10.34.*

* cited by examiner

*Primary Examiner*—James Ketter
*Assistant Examiner*—Konstantina Katcheves
(74) *Attorney, Agent, or Firm*—Kilpatrick Stockton LLP

(57) ABSTRACT

The present invention relates to an improved and efficient method for simultaneous monitoring of abundance of individual mutants of a microbe in mixed populations where insertion of a known transposon in the genome of a microbe such that each mutant caries a single transposon insertion, isolating the genomic DNA of the mixed population of mutants, fragmenting the same with a frequently cutting restriction enzyme, ligating a double standard adapter to the genomic DNA fragments, amplifying the DNA fragments adjoining transposon insertions thereby generating a set of DNA fragments corresponding only to mutated genes resolving the said amplified DNA fragments followed by comparing the intensity of DNA fragments obtained from population of mutants before selection with that obtained from the population subjected to selection and finally sequencing the DNA fragments that change in abundance to identify the mutated genes.

9 Claims, No Drawings

SEQUENCE LISTING

<160> NUMBER OF SEQ ID NOS: 13

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: TaqI
      adapters

<400> SEQUENCE: 1
gacgatgagt cctgag                                                    16

<210> SEQ ID NO 2

```
<211> LENGTH: 14
<212> TYPE: DNA
<213> ORGANISM: Artificial Sequence
<220> FEATURE:
<223> OTHER INFORMATION: Description of Artificial Sequence: TaqI
      adapters

<400> SEQUENCE: 2
cgctcaggac tcat                                                        14

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: TaqI
      adapters

<400> SEQUENCE: 3
atgagtcctg agcga                                                       15

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: TaqI
      adapters

<400> SEQUENCE: 4
ttaacgtgag ttttcgttcc actg                                             24

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: TaqI
      adapters

<400> SEQUENCE: 5
gttccactga gcgtcagacc c                                                21

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: TaqI
      adapters

<400> SEQUENCE: 6
gatgagtcct gagcgaa                                                     17

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: TaqI
      adapters

<400> SEQUENCE: 7
gatgagtcct gagcgac                                                     17

<210> SEQ ID NO 8
<211> LENGTH: 15
```

```
<212> TYPE: DNA
<213> ORGANISM: Artificial Sequence
<220> FEATURE:
<223> OTHER INFORMATION: Description of Artificial Sequence: TaqI
      adapters

<400> SEQUENCE: 8
gatgagtcct gagcg                                                      15

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: TaqI
      adapters

<400> SEQUENCE: 9
gatgagtcct gagcgat                                                    17

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: TaqI
      adapters

<400> SEQUENCE: 10
ctgagcgtca gacccca                                                    17

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: TaqI
      adapters

<400> SEQUENCE: 11
ctgagccgtc agacccccc                                                  18

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: TaqI
      adapters

<400> SEQUENCE: 12
ctgagcgtca gaccccg                                                    17

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: TaqI
      adapters

<400> SEQUENCE: 13
ctgagcgtca gaccct                                                     17
```

METHOD FOR THE SIMULTANEOUS MONITORING OF INDIVIDUAL MUTANTS IN MIXED POPULATIONS

FIELD OF INVENTION

The present invention relates to an improved and efficient method for the simultaneous monitoring of individual mutants of a microbe in mixed populations. Such mutants are distinguished from each other by utilizing the features of the mutated genes themselves. More particularly, by the method of this invention even mutants having subtle quantitative phenotypes, or those without plate screens can be readily monitored quantitatively. This would facilitate in understanding the role of a large number of novel genes identified by the systematic sequencing of microbial genomes, many of which may have only subtle quantitative phenotypes. It would also readily allow the parallel screening of large number of mutated genes for their role under conditions which by their very nature can not have a plate screen; examples include virulence genes of pathogenic microbes, and genes conferring stress tolerance to yeast cells during fermentation in liquid broths. This method has pronounced application in discovering the functions of genes of large number of microbes of medical, industrial and agricultural importance.

BACKGROUND OF THE INVENTION

Isolation and study of mutants impaired in normal cellular phenomena is a standard way to dissect them out at the genetic and biochemical levels, and finally to understand them at the molecular level. The conventional approach to screen mutants is on solid media set in petri-plates. If a mutant has increased growth or survival (positive phenotype) compared to the normal wild-type cells, then it can be easily selected on a plate, even from amongst a lawn of wild-type cells. It can also be enriched from a mixed population in a liquid broth by repeated selection. However, if a mutant cell shows reduced growth or survival (negative phenotype) under the selection condition, then it can not be identified from among a mixed population of cells in liquid broths; yet, a large number of such potential mutant cells can be allowed to form isolated colonies on solid media under non-selective conditions, replica-plated on to selective media and then growth assessed. On the other hand, if there is no plate screen for the phenotype, i.e. if the phenotype does not show up on solid media, then screening by replica plating is not possible. One such example is mutants impaired in stress tolerance under fermentation conditions in liquid broths. Another example is from pathogenic microbes, where to isolate mutants impaired in virulence, one has to individually test potential mutants for pathogenicity in the host organism, which is extremely laborious. Thus, conventional mutant screening methods are very inadequate to identify genes whose mutant phenotype does not show up on solid media.

Four methods have been reported which partially redress this problem, though they remain quite laborious (Hensel et al., 1995, *Science* 269: 400–403; Shoemaker et al., 1996, *Nature genetics* 14: 450–456; Smith et al., 1995, *Proc. Natl. Acad. Sci. USA* 92: 6479–6483; Cormack et al., *Science* 285: 578–582, 1999). In the first method, known as 'signature tagged transposon mutagenesis' (Hensel et al., 1995, *Science* 269: 400–403), random mutants are generated by insertional inactivation of genes by transposons. Prior to this step, the transposons are uniquely marked with random sequence tags. Thus, the mutated genes are tagged with transposons, which in turn are tagged with unique, but random sequence tags; the mutants could be individually monitored in mixed populations by means of the sequence tags. This method was developed and used for identifying bacterial virulence genes. While this is a major advance for screening mutants having negative phenotypes in mixed populations, it suffers from three disadvantages, namely, need for prior introduction of sequence tags, poor sensitivity (only about 100 mutants can be pooled together and screened), and inability to monitor the phenotypes quantitatively.

In the second method known as 'molecular bar coding' (Shoemaker et al., 1996, *Nature genetics* 14: 450–456), each mutated gene is marked with a unique and known sequence tag. This is carried out by replacing the coding sequence of a gene with a selectable marker and a sequence tag, by transformation with PCR (polymerase chain reaction) products having small regions of homology to genes being deleted. Once a large collection of strains are created with each mutated for a single gene and also carrying a unique sequence tag, all of them can be individually monitored in mixed populations by means of their sequence tags. This method is very powerful and can facilitate the quantitative monitoring of the fate of thousands of mutants simultaneously under any selection condition. However, the initial construction of the set of mutants is extremely laborious and time consuming. It is also very expensive, since for each gene to be deleted, a set of long oligos have to be custom synthesized. A prerequisite of this method is that the nucleotide sequence of the genes being deleted should be known. Thus, if the aim is to delete all the genes of a microbe, then the entire sequence of its genome should be determined in the first place. Another important requirement is that the microbe should have a good homologous recombination system for efficiently replacing the native genes with the deleted versions having minimal length of sequence homology. The last requirement may turn out to be insurmountable for a large number of microbes. At present only yeast *Saccharomyces cerevisiae* has been taken up to be studied by this method; the construction of deletion strains is currently being carried out by a large collaboration involving eight American and European laboratories. However, this method is unlikely to be used for studying many important microbes particularly due to the lack of an efficient homologous recombination system, and also due to the cost, time and labor involved.

In the third method a variation of molecular bar coding is used. Here, to begin with, 96 different isogenic parent strains are constructed by introducing unique sequence tags for each (Cormack et al., *Science* 285: 578–582, 1999). These are then mutated by random insertion of a transforming DNA in the genome. Then pools of 96 mutants each are made, where each mutant in the pool has a unique sequence tag. These are then distinguished from each other in mixed populations by hybridization. The limitation of this method is the need for initial introduction of unique sequence tags, and the need for doing large number of hybridizations. In our method there is no need for introduction of sequence tags, making it more economical, less laborious and faster than existing methods.

In the fourth method known as 'genetic footprinting' (Smith et al., 1995, *Proc. Natl. Acad. Sci. USA* 92: 6479–6483), random population of mutants are obtained by transposon mutagenesis. However, the mutants are not uniquely marked with any specific sequence tag. Instead, the fate of each mutant during selection is individually analyzed by PCR, with a gene-specific primer and a transposon specific primer. If a particular PCR product corresponding to a mutant gene is present in the starting population of cells, but absent or reduced in the population subjected to selection, then that would indicate that mutants in that gene do not survive the selection. Though with this method one can identify the genes conferring subtle quantitative phenotypes (Smith et al., 1996, *Science* 274: 2069–2074), it suffers from the need for gene-specific primers and from the need to do individual PCR reactions for each gene of interest. These two requirements make this method extremely laborious and expensive—to comprehensively identify all the genes providing some benefit to a microbe under a selection condition, it is necessary to do several thousand PCR reactions. Since so many reactions have to be done for each selection condition, this method is extremely labor intensive, time consuming and costly. Besides, prior sequence information is necessary for designing gene-specific primers, and thus applicable only to microbes whose genomes are fully sequenced.

Thus, there is a strongly felt need for a method which is less laborious, less time consuming, less demanding in terms of the prior sequence information of the genome, and also less dependent on the homologous recombination system of the organism. Such a method should be capable of detecting quantitative differences in phenotype, and also allow the isolation of mutants which do not have a plate-screen. The conventional mutant screening methods on solid media are deficient in their ability to detect subtle quantitative phenotypes. Besides, as the mutants are essentially kept as isolated colonies, there is not much competition among mutant and wild-type cells for subtle differences in fitness to show up. This can be alleviated if the mutants are screened in mixed population of cells, and different mutants individually monitored by some feature of their genotype. The complete sequencing of several microbial genomes has revealed thousands of novel genes of unknown function. Even in such well studied organisms such as yeast and *E. coli,* about one third of the genes are novel. Obviously, mutants in these genes did not show up in the conventional mutant hunts possibly due to the very nature of the phenotypes conferred by these genes. It appears likely that many of these genes make only subtle/marginal contributions to the fitness of the microbe and thus were missed in conventional screens. Indeed, many of them, when appropriately tested, were found to make subtle, but nevertheless significant contributions to the fitness of the organism (Smith et al., 1996, *Science* 274: 2069–2074; Thatcher et al., 1998, *Proc. Natl. Acad. Sci. USA,* 95: 253–257). Thus, an improved method should be capable of directly identifying mutants that may have only such quantitative phenotypes. Another reason for such a method is that the phenotype of some class of mutants may show up only under some special conditions and not on solid media, e.g. in liquid broths for fermentation, and, in host organisms for mutants impaired in virulence.

OBJECT OF THE INVENTION

The main object of the present invention is to provide an improved and efficient method for the simultaneous monitoring of the abundance of individual mutants of a microbe in mixed populations.

Another object is to use this method to quantitatively trace the abundance of known mutants in mixed populations to follow their fitness under various environmental conditions.

Yet another object is,to use this process to identify novel genes conferring quantitative or difficult-to-screen phenotypes, and thereby assign function to these genes.

DETAILED DESCRIPTION OF THE INVENTION

Accordingly, the present invention provides an improved and efficient method for the simultaneous monitoring of the abundance of individual mutants of a microbe in mixed populations, which comprises, i) generating a population of mutants by the random insertion of a known transposon in the genome of a microbe such that each mutant will preferentially carry only a single transposon insertion, by known methods, ii) isolating the total genomic DNA of the mixed population of mutants by known methods, iii) fragmenting the genomic DNA with a frequently cutting restriction enzyme, by known methods, iv) ligating a double stranded adapter to the genomic DNA fragments, by known methods, v) amplifying only the DNA fragments adjoining transposon insertions by PCR, specifically and quantitatively, using a transposon specific primer and an adapter specific primer, thereby generating a set of DNA fragments corresponding only to the mutated genes of the population of mutants, vi) resolving the amplified DNA fragments according to their size, by known methods, vii) comparing the intensity of the DNA fragments obtained from the population of mutants before selection with that obtained from the population subjected to selection, thereby monitoring the abundance of individual mutants by means of the intensity of the corresponding DNA fragments, to quantitatively follow the abundance of the mutants during selection, and, viii) sequencing the DNA fragments that change in abundance, by known methods, to identify the mutated genes.

In an embodiment of the present invention insertional mutagenesis can be carried out preferably by transposons or by the random insertion of foreign DNA introduced by transformation or by other means.

In another embodiment of the present invention known mutants can be constructed individually, and then mixed and studied together to accurately and quantitatively monitor their phenotypes under various selection conditions, particularly those without any plate screen.

In yet another embodiment of the present invention mutants of selected genes of a microbe homologous to unknown human genes can be constructed, and then mixed and studied together to accurately and quantitatively monitor their phenotypes under various selection conditions, thereby to identify the biological function of these genes.

In yet another embodiment of the present invention the amplified DNA fragments can be labeled to high specific activity and used as hybridization probes to screen colony blots; by screening duplicate blots, one with DNA fragments corresponding to the starting population of mutants, and another with DNA fragments corresponding to the selected population of mutants, clones that change in abundance can be identified and characterized to identify the mutated genes.

In yet another embodiment of the present invention the amplified DNA fragments can be hybridized to gene-filters or DNA chips where DNA corresponding to all the genes of an organism are spotted on filters or glass slides at known locations. By comparing the intensity of the signals obtained with the DNA fragments of mutants before and after selection, one can directly identify the genes important under the selection conditions, particularly for which there is no plate screen.

In yet another embodiment of the present invention this method can be modified to monitor the genes carried on plasmids, and thereby quantitatively monitor the cells carrying such plasmids under varied selection conditions.

In yet another embodiment of the present invention this method can be used to monitor the abundance of different kinds of DNA molecules in a DNA preparation.

The details of the method of the present invention are as follows:

The first step of the process is the generation of a large collection of mutants by insertional inactivation of genes by known transposon tagging methods. In yeast *Saccharomyces cerevisiae* this can be achieved either by Ty mutagenesis (Garfinkel & Strathem, 1991, *Methods in Enzymology* 194: 342–361) or by shuttle mutagenesis (Hoekstra et al., 1991, *Methods in Enzymology* 194: 329–342). Ty mutagenesis uses a modified yeast transposon which can be induced to transpose at a high frequency under the control of a galactose inducible promoter. One limitation of this method is that the Ty elements tend to insert preferentially near tRNA genes. An ideal insertion mutagenesis system is one which randomly inactivates the genes of a microbe without any bias for target sequences. Shuttle mutagenesis, based on a Tn3 based minitransposon, has minimum bias for targets. In this method, yeast genomic DNA, being propagated in *E. coli* as part of a genomic library, is transposon mutagenized and then introduced into yeast by transformation. The transformation is done with a low amount of DNA to ensure that each transformant receives only a single mutation. Since different transformants will receive different mutated regions of the yeast genome, a large collection of such transformants will represent mutants having mutations in almost all the non-essential genes of yeast. Shuttle mutagenesis is applicable to any microbe that can be transformed, and in which gene-disruption can be carried out by homologous recombination. It may also be possible to introduce random insertion mutations into the genome of a microbe by transforming with a foreign DNA lacking any homology to its genome. The transposon (or the foreign DNA), besides mutating the target gene also serves as a sequence tag. However, since all the mutations have the same tag, in the process of the present invention they are distinguished from each other by the sequence features of the mutated genes themselves. To achieve this, the DNA flanking the transposon insertions are selectively and quantitatively amplified as follows.

Genomic DNA from the mixed population of yeast mutants can be isolated by using standard methods (Kaiser et al., 1994, Methods in yeast genetics, Cold spring harbor laboratory press). The average size of the purified genomic DNA should be larger than 20 kb, and it should be free of any deoxyribonuclease contamination. If the DNA is isolated from a mixed population of mutants, each mutant should be represented by tens of thousands of cells so as to reduce sampling error.

The genomic DNA is then cut with a frequently cutting restriction enzyme; the enzyme chosen should be such that most of the DNA fragments obtained should be below 300 bp in size. These are then ligated with a double stranded adapter having one end compatible with the ends generated by the restriction enzyme. This adapter is composed of two oligonucleotides which are not phosphorylated. Besides, their sequence should not be similar to any region of the genome of the microbe being studied. This can be ensured if the entire sequence of the microbe's genome is known; even if the sequence is not known, if a sufficiently long adapter is chosen then it is very likely to be a unique sequence and different from the sequence of the microbe's genome. In the process of the present invention, the adapters used are similar to those used for selective amplification of random restriction fragments (Vos et al., 1995, *Nucleic Acids Research* 23: 4407–4414); however, in the process of this invention the subsequent steps are modified such that instead of random restriction fragments, only those restriction fragments adjoining transposon insertions are amplified, as described below.

Selective amplification of DNA fragments adjoinig transposon insertions is achieved by the use of a primer specific for the terminus of the transposon and a primer specific for the adapter sequence. Besides, the PCR conditions are optimized such that the restriction fragments that carry adapter sequences at both the termini are not amplified: As neither of the oligos of the adapter is phosphorylated, only one of the adapter oligos actually gets ligated to the ends of restriction fragments (through the 5'-phosphate of the restriction fragments). There is a denaturation step prior to the first cycle of PCR which ensures that the unligated adapter oligo falls away; besides, the concentration of template DNA molecules in the reaction is such that they do not renature during the one minute time provided for the annealing of primers during PCR. As the adapter primer used in PCR is of the same sense as the adapter oligo ligated to the ends of restriction fragments, it can not anneal and initiate DNA synthesis unless the complementary strand is first made, which will occur only if there is a binding site for the transposon specific primer. This ensures that only those DNA fragments adjoining transposon insertions get amplified. To further increase the specificity, the annealing temperature is kept as high as possible to prevent mispriming. Besides, nested or semi-nested PCR is done using primers that will anneal and amplify only those DNA fragments that were specifically synthesized during primary PCR, and not the spurious amplification products. These steps together ensure that only those DNA fragments abutting transposon insertions, which actually correspond to the mutated genes, get specifically amplified. The PCR is also designed such that it is quantitative, i.e., the concentration of the amplified DNA fragments is proportional to the concentration of the initial template molecules (which in turn is proportional to the abundance of the mutants). This is ensured by having a low concentration of primers in the reaction, which results in the amplification stopping due to the exhaustion of primers, and not due to the exhaustion of any other component of the PCR reaction. Besides, when multiple products are made, the concentration of any particular product is not so high as to prevent quantitative amplification of that particular product by product-product reannealing. It may also be possible to modify the procedures published for PCR amplifying DNA of an unknown sequence adjoining a region of known sequence, such as suppression PCR (Siebert et al., 1995, *Nucleic Acids Res.* 23: 1087–1088) or ligation mediated PCR methods (Mueller & Wold, 1989, *Science* 246: 780–786; Pfeifer et al., 1989, *Science* 246: 810–813; Palittapongarnpim et al., 1993, *Nucleic Acids Res.* 21: 761–762; Prod'hom et al., 1998, *FEMS Microbiol Lett* 158: 75–81), for this purpose. However, these methods were used for amplifying only a single or a limited number of DNA fragments in a single PCR reaction, without much emphasis on quantitative amplification. Thus, much optimization may be necessary before any of them can be used for quantitative amplification of mutated genes from a mixed population of large number of mutants, as has been done in the process of the present invention.

Once DNA fragments corresponding to the mutated genes are amplified they can be distinguished from each other by their size after resolving them in a high-resolution sequencing gel. This is possible due to the variable position of restriction sites with respect to transposon insertions in different genes. Even if there is some overlap between fragments, they can be resolved if a different restriction enzyme is used for the initial digestion of genomic DNA. By comparing the intensity of DNA fragments obtained before and after selection, the fate of the mutants during selection can be quantitatively monitored. That is, if a DNA band corresponding to a mutant has changed in intensity, then it would indicate that the abundance of the corresponding mutant has changed during selection. If one is dealing with a population of known mutants, then the identity of the band and that of the mutated gene will be known beforehand, and thus the role of the gene under the selection conditions can be quantitatively determined. If one is dealing with a population of unknown mutants, then the identity of the mutated gene can be found out by sequencing the DNA after isolating it from the relevant band and after reamplifying the same. The DNA fragments corresponding to the mutated genes can also be distinguished from each other by hybridizing to colony blots of a genomic library of the microbe under study. By hybridizing duplicate blots, one with the probe made from DNA fragments of the starting population of mutants, and the other with that of the selected population, one can identify the clones whose genes play some role during selection. The identity of the relevant gene can then be found out by sequencing the clone. Similar hybridizations can be carried out with gene filters or DNA chips where DNA corresponding to almost all the genes of a microbe such as yeast Saccharomyces cerevisiae are arrayed at known locations. Thus, from the position of the signal itself one can know the identity of the gene. It may also be possible to further simplify the screening to a single hybridization, by first subtracting the DNA fragments of selected population from that of starting population and using the remaining DNA as probe. Subtraction of DNA fragments can be done by representational difference analysis (Lisitsyn et al., 1993, *Science* 259: 946–951) or by suppression subtractive hybridization (Diatchenko et al., 1996, *Proc. Natl. Acad. Sci. USA* 93: 6025–6030).

The following examples are given by way of illustration of the present invention and should not be construed to limit the scope of the present invention.

EXAMPLE 1

Selective amplification of target sequences from known mutants. To check if PCR amplification is specific, that is only DNA fragments adjoining transposon insertions get amplified and nothing else, experiments were carried out with known mutants. A set of plasmids each carrying a yeast gene mutated with mTn3 was obtained from Michael Snyder of Yale university. These plasmids were prepared by his group as part of a study for analyzing protein production, localization, and function in *Saccharomyces cerevisiae* (Ross-Macdonald et. al., 1997, *Proc. Natl. Acad. Sci. USA* 94: 190–195). These plasmids were purified from *E. coli* by standard methods (Sambrook et al., 1989, "Molecular cloning: a laboratory manual", Cold spring harbor laboratory press), and digested with the restriction enzyme NotI (New England Biolabs). Sites for this enzyme flank the yeast DNA in these plasmids, and thus the yeast DNA along with inserted transposon is released from the vector backbone by this treatment. A *Saccharomyces cerevisiae* strain FY3, an uracil auxotroph, is transformed with each digest individually, by a standard transformation protocol using lithium acetate (Kaiser et al., 1994, "Methods in yeast genetics", Cold spring harbor laboratory press). The transformants become uracil prototrophs by virtue of a wild type URA3 gene engineered as part of the mTn3, and thus can be selected from among a large population of non-transformants. During this process the gene disrupted with the transposon replaces the wild-type gene in the yeast genome.

The yeast transformants, mutated singly for various genes, were grown individually, and genomic DNA was isolated from them by using standard protocols (Kaiser et al., 1994, "Methods in yeast genetics", Cold spring harbor laboratory press). Genomic DNA, 500 ng each, was digested with 20 units of restriction enzyme TaqI (New England Biolabs), in the buffer provided by the manufacturer, at 65° C., for 8 h. The digested DNA samples were then phenol-chloroform extracted, and ethanol precipitated with glycogen as carrier. The DNA pellet was finally dissolved in 9 $\mu$l of 1×TE (10 mM Tris, 1 mM EDTA) buffer, pH 8.0.

The TaqI digested genomic DNA fragments, prepared as above were ligated to TaqI adapters. These adapters are composed of two unphosphorylated oligos of the sequence 5'-GACGATGAGTCCTGAG-3' (SEQ ID NO: 1) and 5'-CGCTCAGGACTCA T-3' (SEQ ID NO: 2) (Vos et al., 1995, *Nucleic Acids Research* 23: 4407–4414). These oligos when annealed together leave a 2 base 5'-overhang at one end which is compatible with the overhangs of the TaqI digested genomic DNA fragments. Ligation was done in 20 $\mu$l volume with 500 ng genomic DNA fragments, 5 $\mu$M adapter, and 100 cohesive end units of T4 DNA Ligase (New England Biolabs) in a buffer containing 15% PEG 8000, 25 mM Tris-Cl, pH 7.8, 5 mM MgCl$_2$, 5 mM dithiothreitol, 500 $\mu$M ATP and 12.5 $\mu$g/ml BSA, at 16° C. for 16 hours. The ligation mixture was diluted to 200 $\mu$l with water and stored frozen until use.

Primary PCR reaction was set up in a 25 $\mu$l volume with 1 $\mu$l of diluted and adapter ligated restriction fragments as template. The PCR mixture contained 20 mM Tris-Cl, pH 9.2, 10 mM KCl, 10 mM ammonium sulphate, 0.1% Triton X-100, 2.5 ng of template DNA, 200 $\mu$M each of the dNTPs, 40 nM TaqI-N primer (5'-ATGAGTCCTGAGCGA-3') (SEQ ID NO: 3), 40 nM Tn3-O2 primer (5'-TTAACGTGAGTTTTCGTTCCACTG-3') (SEQ ID NO: 4), 2 mM MgCl$_2$, and 1 U of Taq DNA polymerase (Promega). The TaqI-N primer is homologous to the TaqI adapter sequences, and the Tn3-O2 primer to the inverted terminal repeats of the mTn3. The reaction mixture without Taq DNA polymerase was topped with a 25 $\mu$l paraffin wax bead and heated at 95° C. for 20 sec, and then allowed to cool for the wax to solidify. The Taq DNA polymerase in 10 $\mu$l of 20 mM Tris-Cl, pH 9.2, 10 mM KCl, 10 mM ammonium sulphate and 0.1% Triton X-100 was overlaid on the wax layer and PCR initiated. As the wax melts at 60° C., the Taq DNA polymerase would mix with the rest of the components and initiate DNA synthesis only above this temperature. At high temperatures the primers anneal only to regions having perfect homology, ensuring that only specific regions are amplified. For PCR amplification, the temperature cycling conditions were as follows: denaturation at 94° C. for 30 seconds, annealing at 65° C. for 30 seconds, and extension at 72° C. for 1 min. This was repeated for 11 more times, but at each subsequent cycle the annealing temperature was reduced by 0.7° C. After this, further amplification was done for 19 cycles, but the annealing temperature was kept constant at 56° C. After the last extension at 72° C., the reactions were incubated at this temperature for an additional 5 min before being terminated.

The PCR products were further amplified and also radio-actively labeled by doing semi-nested PCR. The nested primer Tn3-O1, which is homologous to the mTn3 end of the PCR products, is labeled by T4 polynucleotide kinase (New England Biolabs). A 10 μl labeling reaction contains 70 mM Tris-Cl, pH 7.6, 10 mM MgCl$_2$, 5 mM dithiothreitol, 0.5 mM spermidine-HCl, 25 μCi γ$^{[32]}$P-ATP (3000 Ci/mMol), 4 μM Tn3-O1 and 10 U of T4 polynucleotide kinase, and is incubated at 37° C. for 30 min, and stored frozen until use. A 25 μl semi-nested PCR reaction contained 20 mM Tris-Cl, pH 9.2, 10 mM KCl, 10 mM ammonium sulphate, 0.1% Triton X-100, 1 μl of 10-fold diluted primary PCR product as template, 200 μM each of the dNTPs, 40 nM TaqI-N primer (5'-ATGAGTCCTGAGCGA-3') (SEQ ID NO: 3), 40 nM of labeled Tn3-O1 primer (5'-GTTCCACTGAGCGTCAGACCC-3') (SEQ ID NO: 5), 2 mM MgCl$_2$, and 1 U of Taq DNA polymerase. The enzyme was introduced into the reaction after the first denaturation step and above 60° C. using the wax barrier, as was done with primary PCR. The thermal cycling profile is similar to that of primary PCR, except for the five additional cycles done at the later stage with 56° C. annealing temperature. At the end of amplification, 25 μl of 2×stop solution (95% formamide, 20 mM EDTA, 0.05% bromophenol blue, 0.05% xylene xyanol FF) was added, mixed, heated at 72° C. for 5 min, and chilled in an ice bath. The PCR product was further diluted 20-fold in 1×stop solution, and 5 μl was resolved in a 5% denaturing polyacrylamide gel, as described for sequencing reactions (Sambrook et al., 1989, "Molecular cloning: a laboratory manual", Cold spring, harbor laboratory press). The signals due to the radioactive PCR products were detected by autoradiography.

The PCR products of 17 different mutants were analyzed. Each mutant is expected to give only two DNA bands, one for each flank of the transposon insertion. As the exact position of the transposon insertion with respect to the sequence of the yeast genome is known for each mutant, the position of TaqI restriction sites flanking the transposon insertion and the size of the amplified PCR products can be predicted. Most of the mutants gave two bands each, while some gave only a single band. The predicted size of the missing bands were above 800 bp; presumably, DNA above this size is not efficiently amplified under the conditions used. When the predicted sizes of the PCR products were plotted in a log scale against their mobility in a linear scale all the data fitted in smooth line. This confirmed that the size of the amplified products is as predicted, and amplification is specific.

EXAMPLE 2

Quantitative amplification of target sequences. If the abundance of the mutants are to be monitored by the intensity of the DNA bands corresponding to the mutated genes, then the amplification should be quantitative. That is, the amount of each amplified product should be proportional to the amount of the corresponding target sequence, in a mixed population of targets. To check this, a reconstruction experiment was done where different mutants were mixed in known proportions, and amplification done. Thirty different yeast mutants were individually grown and the extent of growth was determined by measuring the OD of the cultures at 600 nm. The OD of all the cultures were then equalized to 15. Cultures of 25 mutants (7 ml each) were mixed together to get a population of mutants that remain constant in different pools. Cultures of five other mutants (7 ml each) were mixed together to get a population that is deliberately varied in abundance in the different pools. By mixing 25 ml each of the 25-mutant pool with 5, 1.67, 0.5, 0.167, or 0.05 ml of the 5-mutant pool, the abundance of the 5 of the mutants with respect to the other mutants was made 1:1, 1:0.3, 1:0.1, 1:0.03 and 1:0.01, respectively.

Genomic DNA was isolated from all these pools of mutants and processed further for amplification of mutated genes, as described in example 1. At the end of amplification, equal volume of 2×stop solution (95% formamide, 20 mM EDTA, 0.05% bromophenol blue, 0.05% xylene xyanol FF) was added to the reactions, mixed, heated at 72° C. for 5 min, and chilled in an ice bath. Five μl each of the PCR products was resolved in a 5% denaturing polyacrylamide gel and the radioactive signals detected by autoradiography. A comparison of the intensity of the amplified DNA bands showed that those corresponding to the five mutants that were deliberately reduced were proportionately less intense, while the intensity of the bands corresponding to the other mutants remained constant. This result confirmed that amplification is quantitative, and can be used for tracing the abundance of mutants in mixed populations.

EXAMPLE 3

Quantitative monitoring of mixed population of known mutants during selection. To check if mutants can be quantitatively followed under realistic selection conditions, 17 different yeast mutants with transposon insertion mutations in various HSP genes were pooled together and monitored for heat shock tolerance. A yeast strain was singly mutated for DDR48, HSP104, HSP150, HSP35, SOD2, SSA1, SSA2, SSA3, SSA4, SSB1, SSB2, TPS2, UBI4 or YDJ1, by shuttle mutagenesis using mTn3 mutagenezied genes, as described in example 1. For HSP104, SSA4 and SSB2, two different mutants were created for each gene, with the transposon inserted at two different positions in the respective genes. The mutants were grown separately, mixed together at equal proportions and subjected to heat shock at 50° C. for 40 min. The heat shocked cells, and the non-heat shocked control cells were further grown and genomic DNA was isolated. The DNA corresponding to the mutated genes were selectively amplified and analyzed as described in example 1. The DNA corresponding to the mutated gene of each mutant was also analyzed simultaneously, which revealed the identity of the various DNA bands obtained from the mixed population. The DNA bands of HSP104 and TPS2 mutants disappeared in the population subjected to heat shock treatment. This is consistent with the known phenotype of these mutants as HSP104 and TPS2 are necessary for heat shock tolerance of yeast (Sanchez et al., 1992,*EMBO J.* 11: 2357–2364; Elliott et al., 1996, *Genetics* 144, 923–33). The DNA bands corresponding to SSA2 mutants increased in intensity by about two-fold, indicating that mutants in this gene have a higher survival relative to other mutants during heat shock. These results confirm that this method can be used to monitor the abundance of the mutants quantitatively, in mixed populations in liquid broths. Thus, this process will facilitate the identification of genes conferring even only subtle benefits to microbes.

EXAMPLE 4

Selective display of mutated genes of large number of mutants. To check if DNA fragments corresponding to the mutated genes of over one thousand mutants can be simultaneously amplified and displayed, 1200 random yeast mutants obtained after shuttle mutagenesis with mTn3 were analyzed. These were grown in a single pool and genomic DNA was isolated. To selectively amplify DNA corresponding to all the mutated genes, the DNA was cut with TaqI, ligated to adapters, and primary PCR done as described in example 1. Since over 2000 DNA bands are expected if all the DNA fragments flanking transposons are amplified, subsets of them were amplified by nested PCR using primers having additional selective bases at their 3'-termini. The selective primers used were TaqI-A (5'-GATGAGTCCTGAGCGAA-3') (SEQ ID NO: 6), TaqI-C (5'-GATGAGTCCTGAGCGAC-3') (SEQ ID NO: 7), TaqI-G (5'-GATGAGTCCTGAGCG-3') (SEQ ID NO: 8) and TaqI-T (5'-GATGAGTCCTGAGCGAT-3') (SEQ ID NO: 9) homologous to TaqI adapter and having one additional selective base each, and Tn3O-A (5'-CTGAGCGTCAGACCCCA-3') (SEQ ID NO: 10), Tn3O-C (5'-CTGAGCGTCAGACCCCC-3') (SEQ ID NO: 11), Tn3O-G (5'-CTGAGCGTCAGACCCCG-3') (SEQ ID NO: 12) and Tn3O-T (5'-CTGAGCGTCAGACCCCT-3') (SEQ ID NO: 13), homologous to Tn3 termini, but with one additional selective base each.

When a selective TaqI-primer is used in combination with a selective Tn3O-primer in nested PCR, only about one sixteenth of the DNA fragments flanking transposon insertions are expected to be amplified. By using the primers in 16 different combinations, all the DNA fragments corresponding to the mutated genes were amplified and displayed in 16 different lanes. If this is done for control population of mutants and selected population and displayed side-by-side, then DNA fragments that change in intensity can be monitored. Such DNA fragments can be readily isolated from gels, reamplified, and sequenced to determine the identity of the gene mutated in the particular mutant.

Advantages

The key aspect of the process is the selective and quantitative amplification of the DNA fragments corresponding to the mutated genes of numerous mutants, without using any gene specific primers; these DNA fragments are then differentiated from each other according to their size or by hybridization. Since thousands of mutants can be simultaneously monitored after a single. amplification, and since there is no need for prior sequence information, this process is less laborious and less expensive compared to the existing methods. Contrast this with the "genetic footprinting" method (Smith et al, 1995, *Proc. Natl. Acad. Sci. USA* 92: 6479–6483), where to monitor the abundance of each mutant a separate PCR reaction has to be done using a gene-specific primer; besides, to design the primer it is necessary to have prior sequence information of the gene. Our process is also superior to "signature tagged transposon mutagenesis" (Hensel et al, 1995, *Science* 269: 400–403), where the mutants are distinguished from each other by means of the random sequences introduced in the transposons; unlike in this method, in the process of the present invention the mutants are distinguished from each other by the sequence features of the mutated genes themselves, thus alleviating the need for the prior introduction of sequence tags. Besides, in the process of the present invention the abundance of mutants can be monitored quantitatively, facilitating the identification of genes conferring subtle benefits. This process is also more sensitive than "signature tagged transposon mutagenesis" where only about a hundred mutants can be simultaneously monitored. In our method several hundred to thousands of mutants can be monitored together in a mixed population. Though in "molecular bar coding" method (Shoemaker et al, 1996, *Nature genetics* 14: 450–456), thousands of mutants can be monitored quantitatively in a mixed population, it suffers from the need for prior sequence information and prior introduction of unique sequence tag in each mutated gene. Both these requirements may not be easily met in many medically and economically important microbes. In our process there is no need for prior sequence information, or introduction of sequence tags, making it more economical, less laborious and faster than existing methods. Besides, it can also be used for screening mutants in microbes whose genomes are not yet fully sequenced, or which do not have an efficient homologous recombination system for introduction of sequence tags.

In summary, the process provided in the present invention has several advantages.

1. No need for prior genome sequence; thus can be used for studying almost any microbe.
2. No need for gene-specific primers and individual PCR reactions for each gene. Thus less expensive, and less laborious.
3. No need for prior introduction of sequence tags; thus less laborious; also applicable to microbes that do not have an efficient method for introduction of tags.
4. Thousands of mutants can be screened in a single pool; this makes the comparison among mutants very accurate, and less laborious. In pathogenicity studies, handling of dangerous microbes can be enormously reduced if they can be screened in large pools.
5. Phenotypes can be monitored quantitatively; thus, even subtle benefits conferred by the genes can be discovered.
6. Mutants can be monitored in mixed populations; this facilitates the monitoring of mutants under any kind of condition; particularly suited for conditions which can not be reduced to plate screens.

We claim:

1. An improved and efficient process for the simultaneous monitoring of the abundance of individual mutants of a microbe in mixed populations, which comprises, i) generating a population of mutants of a microbe having a genome by the random insertion of a known transposon in the genome of the microbe such that each mutant will preferentially carry only a single transposon insertion, ii) subjecting a first portion of the population of mutants to a desired selection condition, and a second portion to a non-selective condition, iii) isolating total genomic DNA from the selected and non-selected populations of mutants, iv) fragmenting the genomic DNA with a frequently cutting restriction enzyme, iv) ligating a double stranded adapter to the genomic DNA fragments, vi) amplifying only the genomic DNA fragments adjoining transposon insertions by PCR, specifically and quantitatively, using a transposon specific primer lacking a sequence tag and an adapter specific primer, thereby generating a set of DNA fragments corresponding only to the mutated genes of the population of mutants, vii) resolving the amplified DNA fragments according to their size, viii) comparing the intensity of the DNA fragments obtained from the selected population to the intensity of DNA fragments obtained from the non-selected population thereby simultaneously monitoring the abundance of individual mutants by means of the intensity of the corresponding DNA fragments.

2. A method as claimed in claim 1 wherein insertional mutagenesis is carried out by the random insertion of any foreign DNA introduced by transformation, or by other means.

3. A method as claimed in claim 1 wherein the amplified DNA fragments are labeled to high specific activity and used as hybridization probes to screen colony blots and by screening duplicate blots, one with DNA fragments corresponding to the starting population of mutants, and another with DNA fragments corresponding to the selected population of mutants, clones that change in abundance can be identified and characterized to identify the mutated genes.

4. A method as claimed in claim 1 wherein the amplified DNA fragments are labeled to high specific activity and used as hybridization probes to screen gene-filters or DNA chips where DNA corresponding to all the genes of an organism are spotted at known locations and by comparing the intensity of the signals obtained with the DNA fragments of mutants before and after selection, genes playing a role under the selection conditions can be directly identified.

5. A method as claimed in claim 1 wherein mutants in known genes are constructed, and then mixed and studied together to accurately and quantitatively monitor their phenotypes under various selection conditions, to identify their biological role.

6. A method as claimed in claim 1 wherein mutants of selected genes of a microbe homologous to unknown human genes are constructed, and then mixed and studied together to accurately and quantitatively monitor their phenotypes under various selection conditions, thereby to identify the biological function of these genes.

7. A method as claimed in claim 1 wherein the process is modified to monitor the genes carried on plasmids, and thereby quantitatively monitor the cells carrying such plasmids under varied selection conditions.

8. A process as claimed in claim 1 wherein the DNA fragments of non-selected population, which change in abundance in the selected population, are sequenced to identify the genes mutated in the corresponding mutants.

9. A kit for selective amplification of DNA corresponding to the mutated genes of the population of mutants, which comprises:
   - one or more restriction enzymes for fragmenting the genomic DNA of the population of mutants,
   - one or more double stranded adapters for ligating to genomic DNA fragments, and primers corresponding to the adapters, and primers corresponding to transposon DNA lacking a sequence tag and a thermostable DNA polymerase to amplify the DNA fragments corresponding only to the mutated genes of the population of mutants.

* * * * *